United States Patent
Ravishankar et al.

(10) Patent No.: US 10,343,144 B2
(45) Date of Patent: Jul. 9, 2019

(54) MOLECULAR GELATORS FOR CONTAINING OIL SPILLAGE

(71) Applicant: HINDUSTAN PETROLEUM CORPORATION LTD., Mumbai (IN)

(72) Inventors: Raman Ravishankar, Bangalore (IN); Siva Kesava Raju Chinthalapati, Bangalore (IN); Tanmoy Kar, Bangalore (IN); Bhaskar Pramanik, Bangalore (IN); Peddy Venkata Chalapathi Rao, Bangalore (IN); Venkateswarlu Choudary Nettem, Bangalore (IN)

(73) Assignee: Hindustan Petroleum Corporation Ltd., Mumbai (IN)

( * ) Notice: Subject to any disclaimer, the term of this patent is extended or adjusted under 35 U.S.C. 154(b) by 0 days.

(21) Appl. No.: 14/916,025

(22) PCT Filed: Aug. 3, 2015

(86) PCT No.: PCT/IN2015/050079
§ 371 (c)(1),
(2) Date: Mar. 2, 2016

(87) PCT Pub. No.: WO2016/193990
PCT Pub. Date: Dec. 8, 2016

(65) Prior Publication Data
US 2018/0066014 A1   Mar. 8, 2018

(30) Foreign Application Priority Data

May 29, 2015  (IN) .......................... 2098/MUM/2015

(51) Int. Cl.
| | | |
|---|---|---|
| *B01J 20/28* | (2006.01) |
| *C02F 1/68* | (2006.01) |
| *C02F 1/28* | (2006.01) |
| *B01J 20/34* | (2006.01) |
| *B01D 17/02* | (2006.01) |
| *B01J 20/22* | (2006.01) |
| *C09K 3/32* | (2006.01) |
| *C02F 1/40* | (2006.01) |
| *E02B 15/04* | (2006.01) |
| *C02F 101/32* | (2006.01) |
| *E02B 15/00* | (2006.01) |
| *B01J 20/30* | (2006.01) |
| *C07K 5/062* | (2006.01) |

(52) U.S. Cl.
CPC .... *B01J 20/28047* (2013.01); *B01D 17/0202* (2013.01); *B01J 20/22* (2013.01); *B01J 20/3425* (2013.01); *C02F 1/285* (2013.01); *C02F 1/681* (2013.01); *C09K 3/32* (2013.01); *B01J 20/3085* (2013.01); *B01J 20/3491* (2013.01); *C02F 1/40* (2013.01); *C02F 2101/32* (2013.01); *C07K 5/0606* (2013.01); *E02B 15/00* (2013.01); *E02B 15/04* (2013.01)

(58) Field of Classification Search
None
See application file for complete search history.

(56) References Cited

FOREIGN PATENT DOCUMENTS

WO   WO-2013126017 A1 *  8/2013

OTHER PUBLICATIONS

Kar et al. (Langmuir, 2009, 25, 8639-8648).*
Kar et al. (Chemical Communications, 2012, 48, 8389-8391).*
Kar (Chem Comm) Electronic Supplemental Material, pp. S1-S11, 2012.*
Kar, et al. (Langmuir, 2009, 25, 8639-8648). (Year: 2009).*

* cited by examiner

*Primary Examiner* — Clare M Perrin
(74) *Attorney, Agent, or Firm* — Nixon & Vanderhye P.C.

(57) ABSTRACT

In accordance with the present subject matter there is provided peptide-based compounds. methods of making such compounds, gels comprising such compounds, methods of making gels, methods of using such compounds for the containing spill of a hydrocarbon, and methods for reclaiming solvent from gels comprising such compounds.

6 Claims, No Drawings

MOLECULAR GELATORS FOR CONTAINING OIL SPILLAGE

This application is the U.S. national phase of International Application No. PCT/IN2015/050079 filed 3 Aug. 2015, which designated the U.S. and claims priority to IN Patent Application No. 2098/MUM/2015 filed 29 May 2015, the entire contents of each of which are hereby incorporated by reference.

TECHNICAL FIELD

The subject matter described herein in general relates to peptide-based compounds that are able to form gels. The subject matter further relates to methods of making peptide-based compounds, gels including such compounds. The peptide-based compounds can be used to control hydrocarbon spill by gel formation while allowing recovery of said compounds and hydrocarbon.

BACKGROUND

A gel can be defined as a solution in which the solid, also known as a gelator, is meshed to form a rigid or semi-rigid mixture results. Depending on the structural nature of gel networks, gels can be simply divided into chemical gels and physical gels. In the case of chemical gels, the aggregation units at different levels are connected into three-dimensional networks via covalent bonds whereas in physical gels, the molecules of a gelator aggregate into network structure via various non-covalent interactions, which are considerably weaker than covalent bonds.

Physical gelation of water and solvents include polymers, micro- or nano-particles, and low-molecular mass organic compounds (LMMGs). The gels formed by latter are named supramolecular gels or molecular gels and can be used for gelation of oil from oil-water mixtures for oil spill recovery. The spilled oil is transformed from a liquid into semi-solid or rubber-like materials floating on the surface of water by introducing LMMGs into the oil contaminated water.

Jadhav and co-workers have disclosed a new class of sugargelators that can selectively gel (solidify) the oil phase from an oil-water mixture at room temperature. The process for preparation of gelators is easy and environmentally benign. Further, the gelators can be recovered and reused multiple times (Angew. Chem. Int. Ed. 2010, 49, 7695-7698).

Kar and co-workers have disclosed supramolecular hydrogelation of a composite including single walled nanotubes (SWNTs) and amphiphilic dipeptide carboxylates (Chem. Commun., 2012, 48, 8389-8391).

Kar and co-workers have disclosed dipeptide-based long-chain acids/salts capable of efficiently gelating organic solvents and water. The xerogels prepared from the organogels showed time-dependent adsorption of dyes such as crystal violet (Langmuir 2009, 25(15), 8639-8648).

SUMMARY

The present disclosure relates to a compound having the Formula:

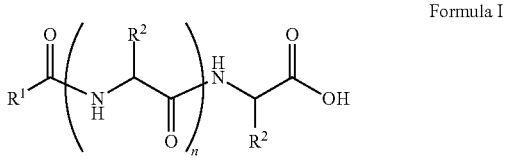

Formula I wherein, $R^1$ is substituted or unsubstituted $C_{10}$ to $C_{25}$ alkyl; $R^2$ is independently substituted $C_1$ to $C_{10}$ alkyl; and n is 1 to 3. The present disclosure also relates to a method of preparing the compound of Formula I.

The present disclosure further relates to a gel comprising a compound of Formula I and a solvent. The present disclosure further relates to a method of producing a gel comprising contacting the compound of Formula I with a solvent.

The present disclosure further relates to a method of containing the spill of a hydrocarbon, the method comprising contacting the hydrocarbon with the compound of Formula I to obtain a gel. The present disclosure further relates to a method of reclaiming solvent from the gel comprising a compound of Formula I and a solvent.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "hydrocarbon(s)" refers to organic compounds that are made of hydrogen and carbon atoms. The source of the hydrocarbons may be from crude oils and refined petroleum products. Crude oil and other petroleum fractions may include compounds with hetero atoms like nitrogen, oxygen, sulfur, halogens and metallic elements along with hydrocarbons.

The term "gel" refers to a colloidal suspension of a solid dispersed in liquid and appear like semi solid.

The term "CRN" means cracked run naptha (mainly comes from the Fluidized Catalytic Cracking (FCC) unit in the refinery).

The term "SRN" means straight run naphtha, which comes from direct distillation of crude oil.

The term "diesel" means a specific fractional distillate of petroleum crude oil between 200° C. and 350° C. at atmospheric pressure.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 140° C. to about 180° C. should be interpreted to include not only the explicitly recited limits of about 140° C. to about 180° C., but also to include sub-ranges, such as 145° C. to 155° C., 150° C. to 170° C., and so forth, as well as individual amounts, including fractional amounts, within the specified ranges, such as 142.2° C., 140.6° C., and 141.3° C., for example.

The present disclosure relates to a class of amphiphilic gelators which can be used for dual purpose as oil or hydrocarbon removal from water. These absorbed hydrocarbons can be easily recovered from the gel including the amphiphilic gelators and oil by heating the gel. The gelators have the potential for selective extraction of oil in water systems and water in oil systems. In one implementation, the present disclosure relates to a compound having the Formula:

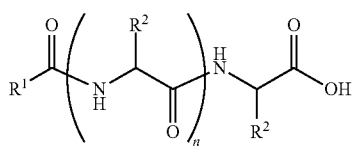

Formula I wherein, $R^1$ is substituted or unsubstituted $C_{10}$ to $C_{25}$ alkyl; $R^2$ is independently substituted $C_1$ to $C_{10}$ alkyl; and n is 1 to 3.

The present disclosure also relates to a method of preparing the compound of Formula I.

The molecular gelators of Formula I can be used for the containment of spilled refinery products such as straight run naphtha, gasoline, diesel fractions and crude oil individually and as a mixture of oil and water emulsion.

The compounds of Formula I can be used for remediation of a release of spilled crude oil or hydrocarbon.

In one implementation, the present disclosure relates to a compound having the Formula:

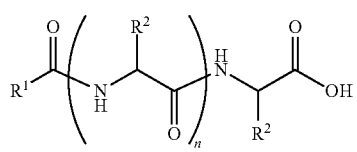

Formula I wherein, $R^1$ is unsubstituted $C_{10}$ to $C_{25}$ alkyl; $R^2$ is independently substituted $C_1$ to $C_{10}$ alkyl; and n is 1 to 3.

In another implementation, the present disclosure relates to a compound having the Formula:

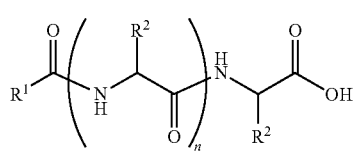

Formula I wherein, $R^1$ is unsubstituted $C_{13}$ to $C_{18}$ alkyl; $R^2$ is independently substituted $C_1$ to $C_{10}$ alkyl; and n is 1 to 3.

In yet another implementation, the present disclosure relates to a compound having the Formula:

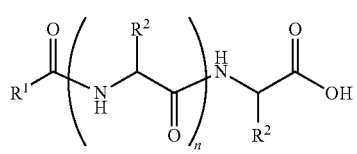

Formula I wherein, $R^1$ is unsubstituted $C_{15}$ alkyl; $R^2$ is independently substituted $C_1$ to $C_{10}$ alkyl; and n is 1 to 3.

In one implementation, the present disclosure relates to a compound having the Formula:

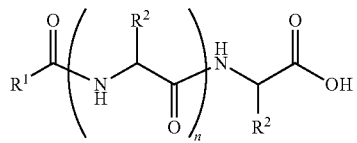

Formula I wherein, $R^1$ is substituted or unsubstituted $C_{10}$ to $C_{25}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3.

In one implementation, the present disclosure relates to a compound having the Formula:

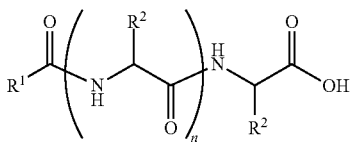

Formula I wherein, $R^1$ is unsubstituted $C_{10}$ to $C_{25}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3.

In another implementation, the present disclosure relates to a compound having the Formula:

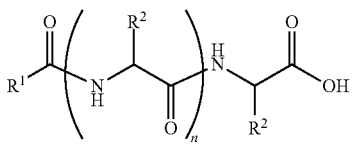

Formula I wherein, $R^1$ is unsubstituted $C_{13}$ to $C_{18}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3.

In yet another implementation, the present disclosure relates to a compound having the Formula:

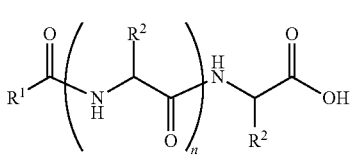

Formula I wherein, $R^1$ is unsubstituted $C_{15}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3.

In one implementation, the present disclosure relates to a compound having the Formula:

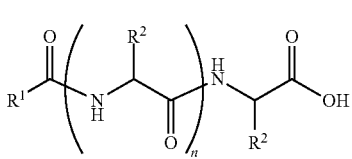

Formula I wherein, $R^1$ is substituted or unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 3.

In one implementation, the present disclosure relates to a compound having the Formula:

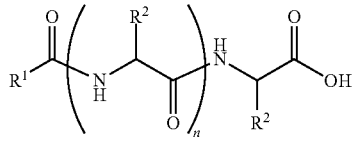

Formula I wherein, $R^1$ is unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 3.

In another implementation, the present disclosure relates to a compound having the Formula:

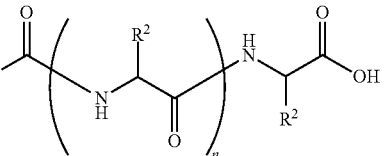

Formula I wherein, $R^1$ is unsubstituted $C_{13}$ to $C_{18}$ alkyl; wherein $R^2$ is $C_1$ to $C_5$ alkyl substituted with S which is further substituted with $C_1$ to $C_3$ alkyl; and n is 1 to 3.

In yet another implementation, the present disclosure relates to a compound having the Formula:

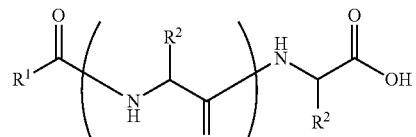

Formula I wherein, $R^1$ is unsubstituted $C_{15}$ alkyl; wherein $R^2$ is $C_1$ to $C_5$ alkyl substituted with S which is further substituted with $C_1$ to $C_3$ alkyl; and n is 1 to 3.

In yet another implementation, the present disclosure relates to a compound having the Formula:

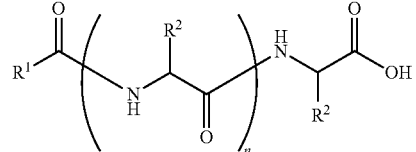

Formula I wherein, $R^1$ is unsubstituted $C_{13}$ to $C_{18}$ alkyl, $R^2$ is $C_1$ to $C_5$ alkyl substituted with S which is further substituted with $C_1$ to $C_3$ alkyl; and n is 1 to 3.

In one implementation, the present disclosure relates to a compound having the Formula:

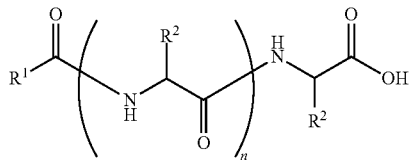
Formula I wherein, $R^1$ is substituted or unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 2.

In one implementation, the present disclosure relates to a compound having the Formula:

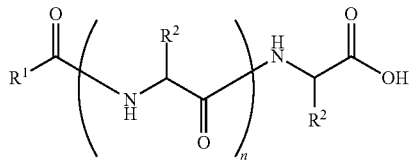
Formula I wherein, $R^1$ is unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 2.

In another implementation, the present disclosure relates to a compound having the Formula:

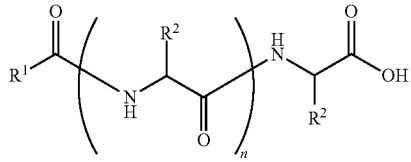
Formula I wherein, $R^1$ is unsubstituted $C_{13}$ to $C_{18}$ alkyl; wherein $R^2$ is $C_1$ to $C_5$ alkyl substituted with S which is further substituted with $C_1$ to $C_3$ alkyl; and n is 1 to 2.

In yet another implementation, the present disclosure relates to a compound having the Formula:

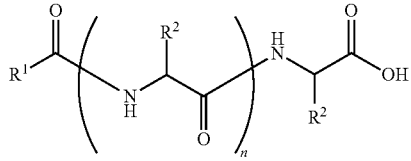
Formula I wherein, $R^1$ is unsubstituted $C_{15}$ alkyl; wherein $R^2$ is $C_1$ to $C_5$ alkyl substituted with S which is further substituted with $C_1$ to $C_3$ alkyl; and n is 1 to 2.

In yet another implementation, the present disclosure relates to a compound having the Formula:

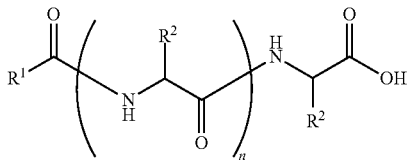
Formula I wherein, $R^1$ is unsubstituted $C_{13}$ to $C_{18}$ alkyl, $R^2$ is $C_1$ to $C_5$ alkyl substituted with S which is further substituted with $C_1$ to $C_3$ alkyl; and n is 1 to 2.

In one implementation, the present disclosure relates to a compound having the Formula:

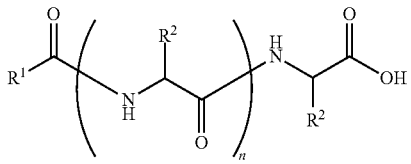
Formula I wherein, $R^1$ is substituted or unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1.

In one implementation, the present disclosure relates to a compound having the Formula:

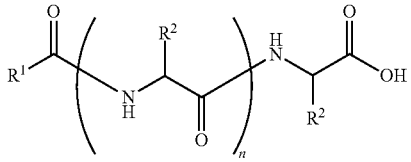
Formula I wherein, $R^1$ is unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1.

In another implementation, the present disclosure relates to a compound having the Formula:

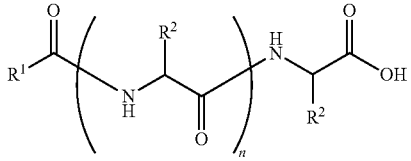
Formula I wherein, $R^1$ is unsubstituted $C_{13}$ to $C_{18}$ alkyl; wherein $R^2$ is $C_1$ to $C_5$ alkyl substituted with S which is further substituted with $C_1$ to $C_3$ alkyl; and n is 1.

In yet another implementation, the present disclosure relates to a compound having the Formula:

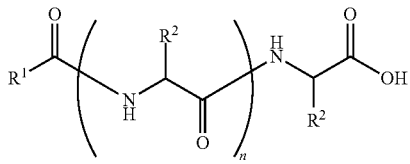

Formula I wherein, $R^1$ is unsubstituted $C_{15}$ alkyl; wherein $R^2$ is $C_1$ to $C_5$ alkyl substituted with S which is further substituted with $C_1$ to $C_3$ alkyl; and n is 1.

In yet another implementation, the present disclosure relates to a compound having the Formula:

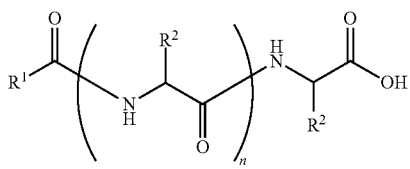

Formula I wherein, $R^1$ is unsubstituted $C_{13}$ to $C_{18}$ alkyl, $R^2$ is $C_1$ to $C_5$ alkyl substituted with S which is further substituted with $C_1$ to $C_3$ alkyl; and n is 1.

In yet another implementation, the present disclosure relates to a compound having the Formula:

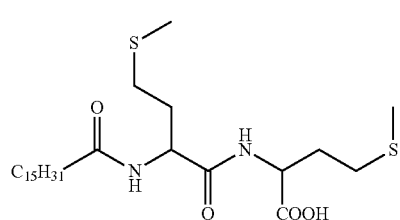

Formula II

The IUPAC name of the compound of Formula II is 4-(methylthio)-2-(4-(methylthio)-2-palmitamidobutanamido) butanoic acid. The present disclosure relates to a method of preparing the compound of Formula I.

In one implementation, the compounds of Formula I and gels synthesized therefrom can be used in such applications as tissue engineering, drug delivery, separation of biomolecules, and stimulus-responsive advanced materials.

The compounds of Formula I can be used to form gels having numerous applications. In one implementation, the compounds of Formula I can be added to one or more solvents in order to produce a gel. In another implementation, the compounds of Formula I can be added to a solvent in order to produce a gel. The present disclosure also relates to method for producing a gel comprising contacting the compound of Formula I with a solvent. The term solvent refers to a polar solvent, non-polar solvent and mixtures thereof. In another implementation, the solvent comprises water, an organic solvent, or mixtures thereof. Solvents can be nonpolar such as, for example, hydrocarbons like pentane, cyclopentane, hexane, cyclohexane, benzene, toluene, xylene, 1,4-dioxane, chloroform, diethyl ether or mixtures thereof. In one implementation, the solvents can be polar, aprotic solvents such as, for example, dichloromethane, tetrahydrofuran, ethyl acetate, acetone, dimethylformamide, acetonitrile, pyridine, carbon disulfide, benzonitrile, or dimethyl sulfoxide. In another implementation, the solvent can be polar protic solvents such as alcohols and carboxylic acids including, but not limited to, formic acid, n-butanol, isopropanol, n-propanol, ethanol, methanol, acetic acid, ethylene glycol, propylene glycol, glycerin, or water. Mixtures of solvents can also be used herein. In one implementation, the solvent can be a mixture of water with a hydrocarbon. In another implementation, the solvent is a hydrocarbon. In another implementation, the solvent is selected from crude oil, or a petroleum product.

The present disclosure also relates to method of containing the spill of a hydrocarbon, the method comprising contacting the hydrocarbon with the compound of Formula I to obtain a gel.

In one implementation, a method of recovering crude oil, or petroleum product from a spill of crude oil, or the petroleum product comprises: (a) forming a gel comprising the crude oil, or the petroleum product and a compound of formula I; (b) collecting the gel; and (c) reclaiming the crude oil or the petroleum product from the gel.

In another implementation, method of reclaiming solvent and a compound of Formula I from the gel comprising the solvent and the compound of Formula I.

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

Synthesis of Compound of Formula II

The compound of Formula II was synthesized according to Scheme 1.

Scheme 1

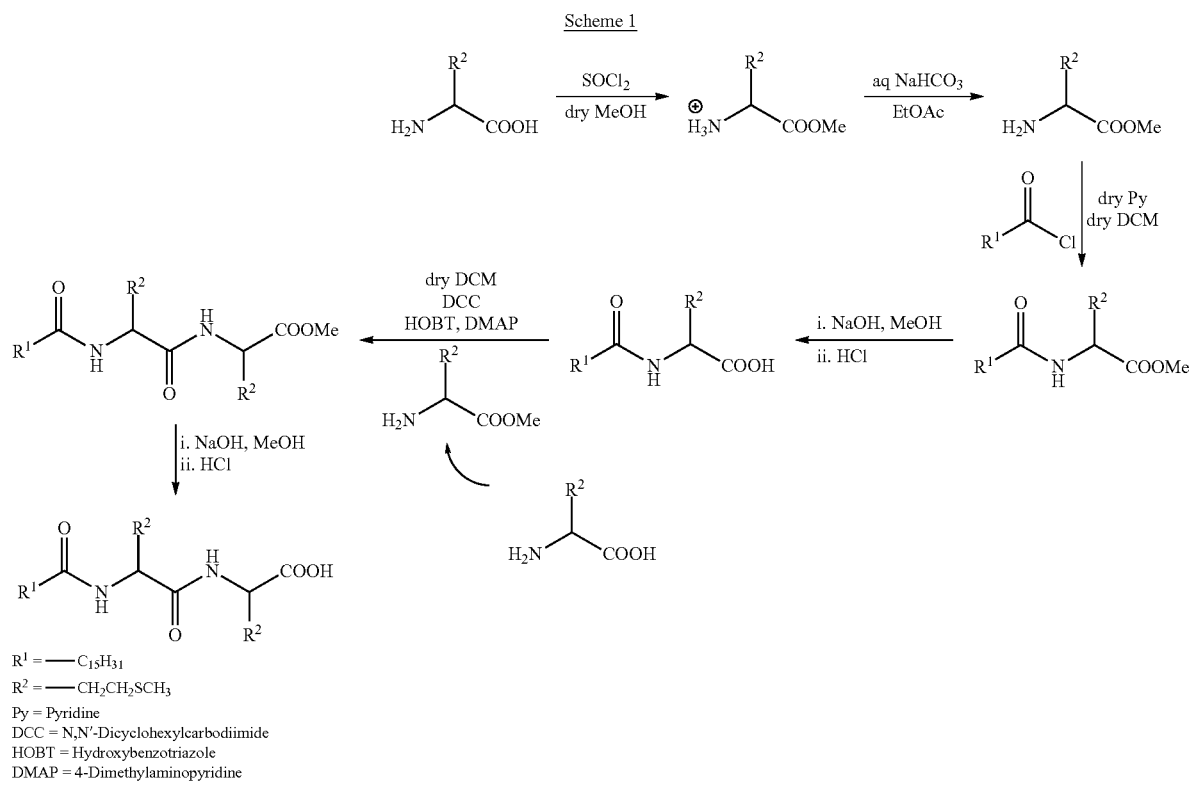

R¹ = —C₁₅H₃₁
R² = —CH₂CH₂SCH₃
Py = Pyridine
DCC = N,N'-Dicyclohexylcarbodiimide
HOBT = Hydroxybenzotriazole
DMAP = 4-Dimethylaminopyridine Methionine (4.47 g, 10 mM) was dissolved in dry MeOH followed by 1.1 equivalent addition of SOCl₂ (2.4 mL, 33 mM) at room temperature. The reaction mixture was then stirred at room temperature for 2 hours. After 2 hours stirring the reaction desired compound was extracted in ethyl acetate after addition of aqueous solution of NaHCO₃. Solvent removal from the organic phase yielded methyl ester of methionine.

The acid chloride of palmitic acid, C₁₅H₃₁COOH (1 equiv, 8.7 g, 30 mM) was dissolved in dry DCM. To this solution methyl ester of Methionine (1.1 equiv, 5.9 g, 33 mM) was added followed by pyridine (1.1 equiv). The reaction mixture was allowed for overnight stirring at room temperature followed by filtration to collect the filtrate. Organic phase was then washed with 1N HCl solution followed by washing with aqueous solution of Na₂CO₃ and then by brine. Solvent removal from the organic phase yielded the ester protected monopeptide compound. The ester protected long chain amide was then purified through column chromatography using 60-120 mesh silica gel and ethyl acetate/hexane as eluent.

The ester protected monopeptide compound (12 g, 30 mM) was hydrolyzed using 1 N NaOH (1.1 equiv) in MeOH for 6 h with stirring at room temperature followed by acidification by 1N HCl. The corresponding carboxylic acid was extracted in ethyl acetate from MeOH solvent. Organic solvent was then removed to obtain the desired product, monopeptide carboxylic acid.

Monopeptide carboxylic acid (11.6 g, 30 mM) was dissolved in dry DCM where methyl ester protected L-amino acid (1.1 equiv, 5.9 g, 33 mM) was added followed by DCC (7.4 g, 33 mM), HOBT (4.8 g, 33 mM) and DMAP (4.4 g, 33 mM). After overnight reaction the organic phase was washed with 1N HCl solution followed by washing with aqueous solution of Na₂CO₃ and then by brine. Organic solvent was then removed to obtain the ester protected dipeptide product. The ester compound is hydrolyzed using 1 N NaOH (1.1 equiv) in MeOH followed by acidification using HCl results the final product. The final product was then purified through column chromatography using 60-120 mesh silica gel and ethyl acetate/toluene as eluent. The product 10.4 g (67% with respect to carboxylic acid) was characterized by proton NMR and mass spectrometry. ¹H NMR (500 MHz, CDCl₃): δ=7.33-7.32 [d, 1H], 6.56-6.54 [d, 1H], 4.74-4.67 [m, 2H], 2.58-2.53 [m, 4H], 2.24-2.21 [m, 3H], 2.11-2.06 [m, 8H], 2.05-1.96 [m, 1H], 1.63-1.61 [m, 2H], 1.28-1.24 [m, 24H], 0.89-0.86 [m, 3H]; E.A: calculated for C₂₆H₅₀N₂O₄S₂: C, 60.19; H, 9.71; N, 5.40. Found: 60.10; 9.79; 5.33; ESI-MS: m/z: 541.4296 (M⁺=C₂₆H₅₀N₂O₄S₂Na⁺), m/z (calculated): 541.3065 (M⁺=C₂₆H₅₀N₂S₂Na⁺).

Example 2

Gelation Study with Crude Oil

In a typical procedure, 10 mg of the gelator compound of Formula II was added to 0.5 ml of crude oil in a glass vial with an internal diameter (i.d.) of 10 mm. The mixture was warmed gently to dissolve the solid compound in crude oil. Then the solution was allowed to cool slowly to room temperature without disturbance. After few minutes, the solid aggregate mass was found to be stable to inversion of the glass vial, and then the compound was recognized to form a gel.

To calculate minimum gelation concentration (MGC), gelator was added gradually from 1 mg to higher amount in required solvent/oil (0.5 ml) and the above process (heating and cooling) was repeated until gel was formed.

Gel melting temperature was determined by typical tube inversion method. The vial containing the gel, as prepared above was immersed in the oil-bath 'upside down' and slowly heated. The temperature at which the viscous gel melted down was recorded as $T_{gel}$.

Gelation Study with CRN:

The gelation process for crude oil was repeated but taking 5 mg of CRN (Table 1).

Gelation Study with SRN:

The gelation process for crude oil was repeated but taking but taking 4 mg of SRN (Table 1).

Gelation Study with Diesel:

The gelation process for crude oil was repeated but taking but taking 5 mg of Diesel oil (as reported in Table 1).

TABLE 1

Gelation abilities of compound of Formula II in different hydrocarbons

| Liquids | Amount of oil (ml) | Weight of gelator (mg) | MGC (%, w/v) | $T_{gel}$ (° C.) |
|---|---|---|---|---|
| Crude | 0.5 | 10 | 2 | 90 |
| CRN | 0.5 | 5 | 1 | 85 |
| SRN | 0.5 | 4 | 0.8 | 80 |
| Diesel | 0.5 | 5 | 1 | 82 |

All these four oil samples were converted to the gel phase using very less amount of the gelator where the minimum gelation concentration (MCG) vary from 0.8 to 1 w/v % for different oil cuts. This work actually is the first example citing gelation of crude oil by amino acid based gelator compound and gelation of the crude oil demands higher MCG (2 w/v %) than the cuts. From the table it is quite evident that best gelation ability of the gelator is exhibited for SRN followed by CRN/diesel and crude oil Example 3

Selective Gelation of Crude Oil from a Biphasic Mixture of Oil and Water

In a typical procedure, 0.5 mL of crude oil and 0.5 mL of water were taken in a sample tube to which 10 mg of the gelator compound of Formula II (as required to attain at least MGC) was added (Table 2). The gelator was then solubilized in this two-phase solution by heating. After the mixture was cooled to room temperature, the crude oil layer was gelated, keeping the water layer intact in the liquid state.

Selective Gelation of CRN from a Biphasic Mixture of Oil and Water:

The gelation process was repeated as that of crude oil but taking 6 mg of CRN (as reported in Table 2) instead of crude oil.

Selective Gelation of SRN from a Biphasic Mixture of Oil and Water:

The gelation process was repeated as that of crude oil but taking 5 mg of SRN (as reported in Table 2) instead of crude oil.

Selective Gelation of Diesel from a Biphasic Mixture of Oil and Water:

The gelation process was repeated as that of crude oil but taking 6 mg of Diesel oil (as reported in Table 2) instead of crude oil.

TABLE 2

Gelation abilities of compound of Formula II in various oil-water mixture

| Liquids | Amount of oil (ml) | Weight of gelator (mg) | Amount of aq phase (ml) | MGC (%, w/v) |
|---|---|---|---|---|
| Crude-water | 0.5 | 10 | 0.5 | 2 |
| CRN-Water | 0.5 | 6 | 0.5 | 1.2 |
| SRN-Water | 0.5 | 5 | 0.5 | 1 |
| Diesel-Water | 0.5 | 6 | 0.5 | 1.2 |

This table signifies that the gelator compound can selectively and effectively convert the oil phase into the gel phase in oil-water mixture. Presence of water demands more gelator compound for gelation as the minimum gelation concentration (MCG) in presence of water is little bit higher than that of previous cases (in absence of water). Here also, the gelation ability of the gelator is superior for SRN than other oils.

Example 4

Selective Gelation of Crude Oil from a Biphasic Mixture of Oil and Salt Solution:

In a typical procedure, 0.5 mL of crude oil and 0.5 mL of 3.5% of NaCl solution (equivalent salt concentration to that of sea water) were taken in a sample tube to which 10 mg of the gelator compound of Formula II was added (Table 3). The gelator was then solubilized in this two-phase solution by heating. After the mixture was cooled to room temperature, the crude oil layer was gelated, keeping the water layer intact in the liquid state.

Selective Gelation of CRN from a Biphasic Mixture of Oil and Salt Solution:

Gelation process mentioned above with crude oil was repeated with 6 mg of CRN (as reported in Table 3).

Selective Gelation of SRN from a Biphasic Mixture of Oil and Salt Solution:

Gelation process mentioned above with crude oil was repeated with 5 mg of SRN (as reported in Table 3).

Selective Gelation of Diesel from a Biphasic Mixture of Oil and Salt Solution:

Gelation process mentioned above with crude oil was repeated with 6 mg of Diesel oil (as reported in Table 3).

TABLE 3

Gelation abilities of compound of formula II in various oil-sea water mixture

| Liquids | Amount of oil (ml) | Weight of gelator (mg) | Amount of aq phase (ml) | MGC (%, w/v) |
|---|---|---|---|---|
| Crude-Sea Water | 0.5 | 10 | 0.5 | 2 |
| CRN-Sea Water | 0.5 | 6 | 0.5 | 1.2 |
| SRN-Sea Water | 0.5 | 5 | 0.5 | 1 |
| Diesel-Sea water | 0.5 | 6 | 0.5 | 1.2 |

Example 5

Oil Spill Recovery:

Oil spill recovery was performed taking 10 ml of SRN over 20 ml of water. An ethanolic solution of the compound of Formula II (0.25 g in 5 mL of Ethanol, 5 w/v %; only 2.5 ml of the ethanolic solution was used for 10 ml of SRN) was added to the SRN-water mixture and allowed to stand for about 15 min where SRN phase was transformed to the gel keeping the water layer intact in the liquid state. The gel phase was filtered off and processed to recover the oil.

Example 6

Reclaiming Solvent from Gel 10 ml of SRN was transformed into gel phase using 80 mg of compound of Formula II. The gel was then subjected to vacuum distillation for oil phase recovery. After successful distillation 8.9 ml of SRN was recovered leaving white powder of the gelator compound with 89% of solvent recovery. The vacuum distillation was carried out at 60° C. for 1 hour.

Advantages Gained in the Example Illustrative Process in this Subject Matter:

Environmentally benign amino acid based phase selective gelator has been developed for oil phase gelation from a mixture of oil and water. The gelators efficiently work even at a very low concentration and at room temperature. The gelators find application in marine oil spill recovery. Oil from the gel can be recovered and gel can be recycled and reused for number of cycles without loss of activity Although the subject matter has been described in considerable detail with reference to certain examples and implementations thereof, other implementations are possible. As such, the spirit and scope of the appended claims should not be limited to the description of the preferred examples and implementations contained therein.

We claim:

1. A method of containing a spill of a hydrocarbon, the method comprising:
    contacting the hydrocarbon with a compound having a Formula:

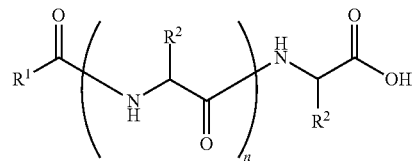

Formula I wherein,
    $R^1$ is substituted or unsubstituted $C_{10}$ to $C_{25}$ alkyl;
    $R^2$ is independently substituted $C_1$ to $C_{10}$ alkyl, substituted with a heteroatom selected from O, N and S, wherein the heteroatom is substituted with C1 to C3 alkyl; and
    n is 1 to 3,
to obtain a gel.

2. The method as claimed in claim 1, wherein $R^1$ is unsubstituted $C_{10}$ to $C_{25}$ alkyl.

3. The method as claimed in claim 1, wherein $R^1$ is unsubstituted $C_{13}$ to $C_{18}$ alkyl.

4. The method as claimed in claim 1, wherein $R^1$ is unsubstituted $C_{15}$ alkyl.

5. The method as claimed in claim 1, wherein $R^2$ is $C_1$ to $C_5$ alkyl substituted with S, wherein the S is further substituted with $C_1$ to $C_3$ alkyl.

6. The method as claimed in claim 1, wherein $R^1$ is unsubstituted $C_{13}$ to $C_{18}$ alkyl, $R^2$ is $C_1$ to $C_5$ alkyl substituted with S, wherein the S is further substituted with $C_1$ to $C_3$ alkyl.

* * * * *